US009920350B2

(12) United States Patent
Binsfeld et al.

(10) Patent No.: US 9,920,350 B2
(45) Date of Patent: *Mar. 20, 2018

(54) METHOD OF DETECTING A SALMONELLA MICROORGANISM

(71) Applicant: 3M INNOVATIVE PROPERTIES COMPANY, St. Paul, MN (US)

(72) Inventors: Chirstine A. Binsfeld, Woodbury, MN (US); Patrick A. Mach, Shorewood, MN (US); Mara S. Celt, Red Wing, MN (US); Adam J. Stanenas, Cottage Grove, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/368,711

(22) PCT Filed: Dec. 19, 2012

(86) PCT No.: PCT/US2012/070580
§ 371 (c)(1),
(2) Date: Jun. 25, 2014

(87) PCT Pub. No.: WO2013/101590
PCT Pub. Date: Jul. 4, 2013

(65) Prior Publication Data
US 2015/0031075 A1    Jan. 29, 2015

Related U.S. Application Data

(60) Provisional application No. 61/580,849, filed on Dec. 28, 2011.

(51) Int. Cl.
*C12Q 1/10* (2006.01)
*C12Q 1/04* (2006.01)

(52) U.S. Cl.
CPC ............... *C12Q 1/10* (2013.01); *C12Q 1/045* (2013.01); *G01N 2333/255* (2013.01)

(58) Field of Classification Search
CPC . C12Q 1/10; C12Q 1/045; C12Q 1/04; C12Q 1/34; C12Q 1/44; C12Q 1/6806; C12Q 1/689; C12N 1/20; C12N 15/1003; C12N 15/1013; C12N 1/06; G01N 2333/255
See application file for complete search history.

(56) References Cited

U.S. PATENT DOCUMENTS

| | | |
|---|---|---|
| 4,565,783 A | 1/1986 | Hansen et al. |
| 5,601,998 A | 2/1997 | Mach et al. |
| 5,681,712 A | 10/1997 | Nelson |
| 5,726,031 A | 3/1998 | Roth et al. |
| 5,786,167 A | 7/1998 | Tuompo et al. |
| 5,871,944 A | 2/1999 | Miller et al. |
| 6,022,682 A | 2/2000 | Mach et al. |
| 6,243,486 B1 | 6/2001 | Weiss |
| 6,265,203 B1 | 7/2001 | Ushiyama |
| 6,638,755 B1 | 10/2003 | Mizuochi et al. |
| 7,150,977 B2 | 12/2006 | Restaino |
| 7,351,574 B2 | 4/2008 | Vent |
| 7,496,225 B2 | 2/2009 | Graessle et al. |
| 2004/0029212 A1 | 2/2004 | Rodriguez Martinez et al. |

FOREIGN PATENT DOCUMENTS

| | | |
|---|---|---|
| JP | 52-051086 | 4/1977 |
| WO | WO 1996/30543 | 10/1996 |
| WO | WO 1998/55644 | 12/1998 |
| WO | WO 2007/017601 | 2/2007 |
| WO | WO 2010/079025 | 7/2010 |
| WO | WO 2012/092181 | 7/2012 |
| WO | WO 2012/161992 | 11/2012 |
| WO | WO 2013/101530 | 7/2013 |

OTHER PUBLICATIONS

Tan W. et al., Automated detection of *Salmonella* spp. in foods, Journal of Microbiological Methods, 1999, vol. 37, pp. 87-91.*
Biokar Diagnostics—XLT4 AGAR—A technical bulletin, Jun. 2009, published on the web at—www.dongnamlab.com/.../XLT4_agar_TDS_BK156_BM036_v7.pdf, pp. 1-4.*
Manafi M. et al., "Fluorogenic and chromogenic substrates used in bacterial diagnostics", Microbiological Reviews, 1991, vol. 55, No. 3, pp. 335-348.*
Pickett M.J. et al., "b-Galactosidase for distinguishing between Citrobacter and *Salmonella*", Applied Microbiology, 1966, vol. 14, No. 3, pp. 178-182.*
Tryland I. et al., "Enzyme Characteristics of b-D-Galactosidase- and b-D-Glucuronidase-Positive Bacteria and Their Interference in Rapid Methods for Detection of Waterborne Coliforms and *Escherichia coli*", Applied and Environmental Microbiology, Mar. 1998, vol. 64, No. 3, pp. 1018-1023.*
Xu, E. et al.; "Study on the Method of Rapidly Detecting the Number of Coliforms"; Journal of Nanchang University (Natural Science); vol. 25, No. 4, 2001; pp. 339-343.
Yang, B. et al.; "Progress on Studies of Mechanism of Antibiotic Resistance of *Salmonella*"; Microbiology; vol. 35, No. 9; 2008; pp. 1479-1484.
Bulmash, J. et al.; "Lactose and Sulfide Reactions of an Aberrant *Salmonella* Strain"; Journal of Bacteriology; vol. 89. No. 1; 1965; p. 259.
Chevalier, P. et al.; "X-α-Gal-based medium for simultaneous enumeration of bifidobacteria and lactic acid bacteria in milk"; Journal of Microbiological Methods; vol. 13; 1991; pp. 75-83.

(Continued)

*Primary Examiner* — Satyendra K Singh (57) ABSTRACT

A composition is provided for detecting a *Salmonella* microorganism in sample. The composition comprises at least one first selective agent that inhibits the growth of Gram-positive microorganisms, a first differential indicator system comprising at least one first differential indicator compound that is converted to a first detectable product by a *Salmonella* microorganism, and a second differential indicator system comprising a second differential indicator compound that is converted by urease enzyme activity to a second detectable product. Optionally, the composition may comprise a third differential indicator system comprising a third differential indicator compound that is converted by a β-galactosidase enzyme activity to a third detectable product. Methods of using the composition to detect a *Salmonella* microorganism are also provided.

11 Claims, 2 Drawing Sheets

(56) References Cited

OTHER PUBLICATIONS

Fookes, M. et al.; "*Salmonella bongori* Provides Insights into the Evolution of the *Salmonellae*"; PLOS Pathogens; vol. 7, No. 8; 2011; e1002191 (16 pgs).

Gonzalez, A.; "Lactose-Fermenting *Salmonella*"; Journal of Bacteriology; vol. 91, No. 4; 1966; pp. 1661-1662.

Littell, A.; "Plating Medium for Differentiating *Salmonella arizonae* from Other *Salmonellae*"; Applied and Environmental Microbiology; vol. 33, No. 2; 1977; pp. 485-487.

Manafi, M.; New developments in chromogenic and fluorogenic culture media:; International Journal of Food Microbiology; vol. 60; 2000; pp. 205-218 (XP-002177549).

Matsen, J. et al.; "Characterization of Indole-Positive *Proteus mirabilis*"; Applied Microbiology; vol. 23, No. 3; 1972; pp. 592-594.

Perry, J. et al.; "ABC Medium, a New Chromogenic Agar for Selective Isolation of *Salmonella* spp."; Journal of Clinical Microbiology; vol. 37, No. 3; 1999; pp. 766-768 (XP-002154638).

Rambach, A.; "New Plate Medium for Facilitated Differentation of *Salmonella* spp. from *Proteus* spp. and Other Enteric Bacteria", Applied and Environmental Microbiology; vol. 56, No. 1; 1990; pp. 301-303.

Presentation by Ana Paccagnella entitled "Naming the *Salmonellae*: all you wanted to know about Saintpaul, Sandiego, Heidelberg, Muenchen and other destinations"; 2005; 36 pgs.

Brochure entitled "Interpretation Guide—3M Petrifilm™ Enterobacteriaceae Count Plate"; from 3M Food Safety; 2010; No. 70-2008-8668-0 (90.2)ii (6 pgs).

Brochure entitled "Urea Agar Base (7226)"; from NEOGEN Corporation; 2010; No. PI 7226, Rev. 4; (3 pgs).

Junillon, T. et al.; "Simplified detection of food-borne pathogens: An in situ high affinity capture and staining concept"; Journal of Microbiological Methods; vol. 91. No. 3; 2012; pp. 501-505.

* cited by examiner

Fig. 1

Fig. 2

METHOD OF DETECTING A SALMONELLA MICROORGANISM

CROSS REFERENCE TO RELATED APPLICATIONS

This application is a national stage filing under 35 U.S.C. 371 of PCT/US2012/070580, filed Dec. 19, 2012, which claims priority to U.S. Provisional Patent Application No. 61/580,849, filed Dec. 28, 2011, the disclosure of which is incorporated by reference in its entirety herein.

BACKGROUND

The family Enterobacteriaceae includes a large number of metabolically-diverse, facultatively-anaerobic bacteria that are capable of fermenting sugars (e.g., glucose) to lactic acid and/or other acidic end products. The family includes several well-known human pathogens such as *Escherichia coli*, several subspecies of *Salmonella*, *Yersinia pestis*, several species of *Klebsiella*, and several species of *Shigella*.

The genus *Salmonella* includes two species, *S. enterica* and *S. bongori*, that include subspecies *capable* of causing illness in humans. Some of the pathogenic Salmonellae can be transmitted to humans via the ingestion of contaminated food or beverages. The detection of *Salmonella* microorganisms in food samples can be difficult due to the presence of relatively low numbers of the *Salmonella* microorganisms in the sample, the presence of relatively high numbers of closely-related non-*Salmonella* enteric microorganisms in the sample, and/or the presence of non-microorganism materials (e.g., food particles or soluble chemicals) in the sample that can interfere with the growth or detection of the *Salmonella* microorganisms.

A variety of selective and/or differential microbiological culture media have been developed to detect *Salmonella* microorganisms in a sample and to distinguish them from one or more non-*Salmonella* microorganisms. Typically, these culture media include a selective agent that inhibits the growth of non-enteric microorganisms. In addition, many of these culture media rely on one or more differential indicator systems to distinguish between *Salmonella* and non-*Salmonella* microorganisms.

In spite of the variety of microbiological culture media to detect *Salmonella* microorganisms in a sample, there remains a need for improved methods to detect a *Salmonella* microorganism in a sample.

SUMMARY

In general, the present disclosure relates to compositions and methods to detect a presence or absence of a *Salmonella* microorganism in a test sample. In particular, the composition facilitates the growth of *Salmonella* microorganisms and includes at least one selective agent that inhibits the growth of Gram-positive microorganisms. Moreover, the composition includes at least two differential indicator systems. At least one of the differential indicator systems positively differentiates *Salmonella* microorganisms from non-*Salmonella* microorganisms and at least one of the differential indicator systems negatively differentiates *Salmonella* microorganisms from non-*Salmonella* microorganisms.

In one aspect, the present disclosure provides a composition. The composition can comprise a semisolid culture medium that includes a gelling agent, at least one first selective agent that inhibits the growth of Gram-positive microorganisms, a first differential indicator system comprising at least one first differential indicator compound, and a second differential indicator system comprising a second differential indicator compound that is converted by urease enzyme activity to a second detectable product. The first differential indicator compound is capable of being converted by a plurality of members of the genus *Salmonella* to a first detectable product. The first differential indicator compound cannot be converted to the first detectable product by a plurality of genera of non-*Salmonella*, Gram-negative enteric microorganisms that form detectable colonies in and/or on the culture medium.

In any embodiment of the composition, the first differential indicator compound can comprise a compound selected from the group consisting of melibiose, 2-deoxy-D-ribose, mannitol, L-arabinose, dulcitol, maltose, L-rhamnose, trehalose, D-xylose, sorbitol, and a combination of any two or more of the foregoing compounds. In any of the above embodiments, the composition further can comprise buffer reagent. The buffer reagent can be selected from the group consisting of MOPS, a phosphate salt, TES, HEPES, and combinations thereof.

In any of the above embodiments, the composition further can comprise a third differential indicator system comprising a third differential indicator compound that is converted by a β-galactosidase enzyme activity to a third detectable product. In any embodiment, the third differential indicator compound can comprise a chromogenic enzyme substrate. In any embodiment, the third differential indicator compound can be selected from the group consisting of 5-bromo-4-chloro-3-indolyl-β-D-galactopyranoside; 5-bromo-6-chloro-3-indolyl-β-D-galactopyranoside; o-nitrophenyl-β-D-galactopyranoside; p-nitrophenyl-β-D-galactopyranoside; 3,4-cyclohexenoesculetin-β-D-galactopyranoside; and 6-chloro-3-indolyl-β-D-galactopyranoside.

In any of the above embodiments, the at least one first selective agent can be selected from the group consisting of bile salts, cholic acid, deoxycholic acid, crystal violet or a combination of any two or more of the foregoing compounds. In any of the above embodiments, the pH indicator can be selected from the group consisting of phenol red, chlorophenol red, neutral red, bromthymol blue, and bromthymol purple.

In any of the above embodiments, the composition further can comprise at least one second selective agent that inhibits the growth of at least one Gram-negative enteric microorganism that is not a member of the genus *Salmonella*. The at least one second selective agent can be selected from the group consisting of a β-lactam antibiotic, an aminoglycoside antibiotic, a quinolone antibiotic, a sulfa antibiotic, a polymyxin antibiotic, and a combination of any two or more of the foregoing antibiotics; wherein the concentration of the at least one second selective agent is selected to permit the growth of a *Salmonella* microorganism. In any of the above embodiments, the gelling agent is selected from the group consisting of agar, agarose, pectin, gelatin, guar gum, xanthan gum, locust bean gum, hydroxyethylcellulose, carboxymethylcellulose, polyvinyl alcohol, algin, and a combination of any two or more of the foregoing gelling agents.

In another aspect, the present disclosure provides a method of detecting a *Salmonella* microorganism. The method can comprise providing a test sample, a culture device, and the composition of any one of the above embodiments; contacting in the culture device the composition and the test sample to form an inoculated culture device; incubating the inoculated culture device for a first period of time; and observing the culture device to detect a first detectable product, wherein the first detectable product is a first indication of a presence of a *Salmonella* microorganism.

In any embodiment of the method, detecting the first detectable product can comprise observing a reaction of the pH indicator with an acidic compound produced by a bacterium. In any embodiment, the method further can comprise observing the nutrient medium to detect a second detectable product, wherein the second detectable product indicates a presence of a non-*Salmonella* microorganism. Detecting a second detectable product can comprise observing a reaction of the pH indicator with a basic compound produced by a bacterium. In any embodiment, the method further can comprise observing the nutrient medium to detect a third detectable product, wherein the third detectable product indicates a presence of a non-*Salmonella* microorganism. Detecting the third detectable product can comprise detecting a colored product produced by β-galactosidase enzyme activity.

In any of the above embodiments, the method further can comprise providing an article with a confirmatory indicator compound that can be metabolized by a *Salmonella* microorganism to a fourth detectable product, wherein the fourth detectable product can be distinguished from the first detectable product, second detectable product, and third detectable product, if present; contacting the article with the culture medium; incubating the device for a second period of time; and observing the culture device to detect the fourth detectable product; wherein detecting the fourth detectable product juxtaposed with the first detectable product is a second indication of the presence in the sample of a *Salmonella* microorganism.

In any of the above embodiments, the method further can comprise enumerating a number of colonies of a first type of microorganisms. In any embodiment, the method further can comprise enumerating a number of colonies of a second type of microorganisms. In any embodiment of the method, observing the culture device can comprise observing the culture device visually. In any embodiment of the method, observing the culture device can comprise creating an image of the culture device using an imaging device. In any embodiment, the method further can comprise analyzing the image using a processor.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

"*Salmonella* microorganism", as used herein, refers to any microorganism belonging to the genus *Salmonella*.

"Differential indicator system", as used herein, refers to one or more compounds that are used to distinguish two types of microorganisms based upon the microorganism's respective ability to convert at least one of the compounds (referred to herein as a "differential indicator compound") to a detectable product. In some instances, for example, the differential indicator compound (e.g., 2-nitrophenyl-β-D-galactoside) may be converted by a type of microorganism directly to the detectable product (e.g., 2-nitrophenol). In some instances, for example, the differential indicator compound (e.g., 5-bromo-4-chloro-3-indoxyl-α-D-galactopyranoside) may be converted by a type of microorganism to an intermediate product that, in the presence of air can react to form the detectable product (a type of indigo dye). In some instances, for example, the differential indicator compound (e.g., a fermentable carbohydrate such as melibiose) can be converted by a type of microorganism to the detectable product (e.g., lactic acid), which can react with another component of the differential indicator system (e.g., a pH indicator such as chlorophenol red) to cause a detectable color change in the other component.

The terms "comprises" and variations thereof do not have a limiting meaning where these terms appear in the description and claims.

As used herein, "a," "an," "the," "at least one," and "one or more" are used interchangeably. Thus, for example, a microorganism can be interpreted to mean "one or more" microorganisms.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Additional details of these and other embodiments are set forth in the accompanying drawings and the description below. Other features, objects and advantages will become apparent from the description and drawings, and from the claims.

DETAILED DESCRIPTION

The genus *Salmonella* includes two species, *Salmonella enterica* and *Salmonella bongori*. The genetic relatedness of the two species has been studied by Fookes et al. ("*Salmonella bongori* Provides Insights into the Evolution of the Salmonellae", PLOs Pathogens at www.plospathogens.org, 2011, vol. 7, article number e1002191, p 1-16, which is incorporated herein by reference in its entirety). Although subspecies of *S. enterica* are better known than *S. bongori* for their ability to infect and cause disease in humans, *S. bongori* has also been shown to cause human infections. Thus, a test designed to detect potentially-pathogenic *Salmonella* microorganisms should be capable of detecting both species.

The present disclosure generally relates to a method for of detecting *Salmonella* microorganisms in a sample. In particular, the present disclosure relates to compositions and growth-based detection methods that are capable of distinguishing *Salmonella* microorganisms from non-*Salmonella* microorganisms (e.g., *Escherichia coli* and other members of the family Enterobacteriaceae). The inventive method combines a selective growth medium that includes a plurality of differential indicator reagents. Optionally, the method can use an elevated incubation temperature to differentiate *S. bongori* microorganisms from non-*Salmonella* β-D-galactosidase-producing microorganisms.

Growth-based detection and identification of *Salmonella* generally requires the use of biochemical reactions that specifically detect *Salmonella* strains in the presence of non-*Salmonella* microorganisms. Unfortunately, most of the conventional detection systems do not provide for adequate specificity to differentiate *Salmonella* microorganisms from non-*Salmonella* Enterobacteriaceae microorganisms that may be present in the sample. The tests often require additional reagents and procedures (e.g., immunological or genetic tests) to differentiate non-*Salmonella* microorganisms from *Salmonella* microorganisms found in a sample.

Unfortunately, some of the reactions that are commonly used to detect groups of non-*Salmonella* enteric microorganisms (e.g. coliform bacteria) do not negatively-differentiate all *Salmonella* strains. For example, there are some *Salmonella* microorganisms that have the metabolic capability to utilize certain compounds (e.g., melibiose, 2-deoxy-D-ribose, dulcitol, trehalose) as a carbon and/or energy source. In the process of utilizing these compounds, the *Salmonella* microorganisms may produce a detectable end product (i.e., an organic acid). Thus, an indicator system to detect the utilization of these compounds can be used to detect the presence of a *Salmonella* microorganism in a test sample. Most other microorganisms do not possess the same metabolic capabilities. However, some non-*Salmonella* Gram-negative enteric microorganisms may have the ability to utilize the compounds. Therefore, it is desirable to include at least one other indicator system to distinguish the non-*Salmonella* microorganisms from *Salmonella* microorganisms. The other indicator system(s) may serve to positively differentiate *Salmonella* microorganisms from non-*Salmonella* microorganisms (i.e., *Salmonella* microorganisms generally react with the indicator system and non-*Salmonella* microorganisms generally don't react with the indicator system) or may serve to negatively differentiate *Salmonella* microorganisms from non-*Salmonella* microorganisms (i.e., *Salmonella* microorganisms generally don't react with the indicator system and non-*Salmonella* microorganisms generally react with the indicator system).

The inventive composition of the present disclosure includes at least two differential indicator systems that permit the operator to perform a method that distinguishes (i.e., differentiates) a *Salmonella* microorganism from at least two types of non-*Salmonella*, Gram-negative, enteric microorganisms. That is, the composition of the present disclosure positively distinguishes *Salmonella* microorganisms from non-*Salmonella* microorganisms that do not metabolize a first indicator compound and, simultaneously, the composition negatively distinguishes *Salmonella* microorganisms that are unable to metabolize a second differential indicator compound from non-*Salmonella* microorganisms that are capable of metabolizing the second differential indicator compound. The method and composition provides presumptive evidence of a presence or an absence of a *Salmonella* microorganism in a test sample. Moreover, the composition optionally can include a third differential indicator system and/or can be used in a method with a fourth differential indicator system to provide confirmatory evidence of the presence of a *Salmonella* microorganism in the test sample.

The present disclosure provides a composition to detect a *Salmonella* microorganism. The composition comprises a semisolid culture medium that includes a gelling agent, at least one first selective agent that inhibits the growth of Gram-positive microorganisms, a first differential indicator system comprising at least one first differential indicator compound, and a second differential indicator system comprising a second differential indicator compound that is converted by urease enzyme activity to a second detectable product. The at least one first differential indicator compound is capable of being converted by a plurality of members of the genus *Salmonella* to a first detectable product. In addition, the at least one first differential indicator compound cannot be converted by a plurality of genera of non-*Salmonella*, Gram-negative enteric microorganisms that form detectable colonies in and/or on the culture medium.

The culture medium of the present disclosure comprises a gelling agent. The gelling agent may comprise any gelling agent suitable for use in a semisolid microbiological culture medium used to culture a Gram negative enteric microorganism. Non-limiting examples of suitable gelling agents include agar, agarose, pectin, gelatin, guar gum, xanthan gum, locust bean gum, hydroxyethylcellulose, carboxymethylcellulose, polyvinyl alcohol, algin, and a combination of any two or more of the foregoing.

The culture medium of the present disclosure may further comprise a nutrient to facilitate the growth of Gram negative enteric microorganisms. Such nutrients are well known in the art and may include, for example, one or more peptones (e.g., pancreatic digest of casein, peptic digest of animal tissue, peptone, pancreatic digest of gelatin, proteose peptone, and the like) and/or one or more growth supplements (e.g., yeast extract; meat extract (beef/porcine, etc.); a salt of Mg, Mn, and/or Ca; a sugar). The culture medium may comprise other nutrients (e.g. minerals or other components), provided they do not substantially interfere with the function of first differential indicator system, the second differential indicator system, and/or the third differential indicator system, if present.

The culture medium of the present disclosure comprises a first differential indicator system that comprises at least one first differential indicator compound. The first differential indicator system is a differential indicator system that positively differentiates a *Salmonella* microorganism from a plurality of non-*Salmonella* Gram-negative enteric microorganisms. Accordingly, the first differential indicator compound is capable of being converted by a plurality of members of the genus *Salmonella* to a first detectable product. Moreover, the first differential indicator compound is not converted by a plurality of genera of non-*Salmonella*, Gram-negative enteric microorganisms to the first detectable product.

Preferably, the first differential indicator compound can be converted to the first detectable product by microorganism belonging to the species *Salmonella bongori*. More preferably, the first differential indicator compound also is converted to the first detectable product by a *Salmonella* microorganism belonging to a species other than *S. bongori* (e.g., *S. enterica*). In some embodiments, the first differential indicator system may comprise a first differential indicator compound that can be converted to the first detectable product by at least one non-*Salmonella* enteric microorganism. Advantageously, the second differential indicator system and/or the third differential indicator system, if present, can be used to negatively differentiate a non-*Salmonella* microorganism growing in or on the composition from a member of the genus *Salmonella*.

In some embodiments, the first differential indicator compound is a nutrient (e.g., a carbohydrate) that can be converted (e.g., via fermentation) by a microorganism (e.g., a microorganism belonging to the genus *Salmonella*) to a first detectable product (e.g., one or more acidic compound such as lactic acid, for example, and/or a gas such as carbon dioxide and/or hydrogen, for example. A person having ordinary skill in the art will recognize, when the first detectable product is an acidic compound produced by the fermentation of the first differential indicator compound, that the acidic compounds produced by two different microorganisms may be the same acidic compound or they may be different acidic compounds.

In an embodiment wherein an acidic compound is the first detectable product, the first differential indicator system further can comprise a pH indicator. A number of pH indicators to detect acidic compounds produced by bacteria are known in the art. Non-limiting examples of suitable pH indicators include phenol red, chlorophenol red, neutral red, bromthymol blue, and bromthymol purple. In some embodiments wherein the first detectable product comprises a gas, the gas may be detected, for example, by trapping the gas (e.g., by trapping it in a hydrogel in a thin film culture device, as described in the Interpretation Guide for the PETRIFILM Enterobacteriaceae Count Plate, which is incorporated herein by reference in its entirety).

Preferably, in an embodiment wherein the first differential indicator compound comprises a nutrient, the first differential indicator compound is converted to the first detectable product by a plurality of *Salmonella* species and/or subspecies to the first detectable product. More preferably, the first differential indicator comprises a nutrient that is not converted to the first detectable product by many species of Gram-negative, enteric microorganisms that do not belong to the genus *Salmonella*. Even more preferably, the nutrient first differential indicator comprises a nutrient that is not converted to the first detectable product by a non-*Salmonella* microorganism. Non-limiting examples of suitable first differential indicator compounds include a compound selected from the group consisting of melibiose, 2-deoxy-D-ribose, mannitol, L-arabinose, dulcitol, maltose, L-rhamnose, trehalose, D-xylose, sorbitol, and a combination of any two or more of the foregoing compounds.

In some embodiments, the first indicator compound may comprise an enzyme substrate. Suitable enzyme substrates include a chromogenic enzyme substrate or fluorogenic enzyme substrate that is converted (e.g., hydrolyzed by an enzyme) to a first detectable product (e.g. a colored product or a fluorescent product) by a microorganism belonging to the genus *Salmonella*. Preferably, the enzyme substrate is converted to the first detectable product by a microorganism belonging to the species *Salmonella bongori* and by a microorganism belonging to the species *S. enterica*. Non-limiting examples of suitable enzyme substrates include enzyme substrates to detect caprylate esterase enzyme activity or to detect α-galactosidase enzyme activity. Suitable chromogenic enzyme substrates include, for example, an enzyme substrate selected from the group consisting of 5-bromo-6-chloro-3-indolyl caprylate, 4-nitrophenyl caprylate, 2-naphthyl caprylate, 4-methylumbelliferyl caprylate, 5-bromo-4-chloro-3-indoxyl-α-D-galactopyranoside, 6-chloro-3-indoxyl-α-D-galactopyranoside, 5-bromo-6-chloro-3-indoxyl-α-D-galactopyranoside, 1-naphthyl-α-D-galactopyranoside, 2-naphthyl-α-D-galactopyranoside, resorufinyl-α-D-galactopyranoside, 4-nitrophenyl-α-D-galactopyranoside, and 4-methylumbelliferyl-α-D-galactopyranoside, combinations thereof.

The culture medium of the present disclosure comprises a second differential indicator system comprising an indicator of urease enzyme activity. The second differential indicator system is a differential indicator system that negatively differentiates a *Salmonella* microorganism from a plurality of non-*Salmonella* Gram-negative enteric microorganisms. Accordingly, the second differential indicator compound is capable of being converted by a plurality of genera of non-*Salmonella*, Gram-negative enteric microorganisms to the second detectable product. Moreover, the second differential indicator compound is not converted by a plurality of members of the genus *Salmonella* to the second detectable product.

Urease is an enzyme that is found in certain non-*Salmonella* Gram-negative, enteric microorganisms (e.g., certain species belonging to the genera *Proteus, Klebsiella, Morganella, Providencia,* and *Serratia*). Some of these microorganisms (e.g., *Proteus mirabilis*; see, for example, J M Matsen et al., 1972, Appl. Microbiol., vol. 23, pp 592-594, which is incorporated herein by reference in its entirety) are capable of converting one or more of the first differential indicator compounds (e.g., trehalose, xylose) to the first detectable product. Thus, in a differential culture medium containing exclusively the first differential indicator system described herein, it may not be possible to distinguish a *Salmonella* microorganism from one of these non-*Salmonella*, Gram-negative enteric microorganisms. Advantageously, by adding to the culture medium the second differential indicator system, the *Salmonella* microorganisms can be differentiated from non-*Salmonella* microorganisms because *Salmonella* microorganisms typically do not possess urease enzyme activity.

Second differential indicator systems of the present disclosure may comprise urea and a suitable pH indicator (e.g., phenol red, chlorophenol red, neutral red, bromthymol blue, and bromthymol purple or phthalhydrazidylazoacetylacetone). Urease enzyme activity hydrolyzes urea into carbon dioxide and ammonia which, in the presence of water forms ammonium hydroxide. Thus, in some embodiments, the second detectable product comprises an ammonium compound. A microbial colony having urease activity and growing in the presence of urea produces an ammonium compound, which causes the pH of the culture medium surrounding the colony to go up. An appropriate pH indicator present in the culture medium can indicate a resulting pH change typically as a zone or halo encompassing the bacterial colony (e.g., in the case of phenol red as the pH indicator, the colony may be violet-stained and/or the colony may have a violet zone surrounding it). Other indicators of urease enzyme activity may be suitable, including, for example, a fluorogenic urease enzyme substrate (e.g., 3-(1-acetylacetonylazo)phthalhydrazide).

Compositions of the present disclosure further comprise at least one first selective agent to inhibit the growth of Gram-positive microorganisms, thereby reducing the competition for nutrients and facilitating the growth of Gram-negative microorganisms such as members of the genus *Salmonella*. Non-limiting examples of suitable first selective agents include a selective agent selected from the group consisting of an antibiotic, bile salts, bile salts No. 3, cholic acid, deoxycholic acid, crystal violet, sodium chloride, novobiocin, nalidixic acid, streptomycin, polymyxin B), and a combination of any two or more of the foregoing selective agents.

Compositions of the present disclosure optionally may comprise at least one second selective agent to inhibit the growth of at least one-Gram negative enteric microorganism that is not a member of the genus *Salmonella*. In some embodiments, the second selective agent may also inhibit the growth of at least one Gram-positive microorganism.

Advantageously, the second selective agent, in combination with the first selective agent, further inhibits microorganisms (Gram-negative and/or Gram-positive microorganism), thereby reducing the competition for nutrients and facilitating the growth of a *Salmonella* microorganism. In addition, the at least one second selective agent may also substantially prevent the growth of a non-*Salmonella* Gram-negative microorganism that otherwise would convert the first differential compound and/or third differential compound to its respective detectable product. Thus, the second selective agent may reduce the probability of a non-*Salmonella* microorganism growing in or on the composition and being interpreted as a possible *Salmonella* microorganism. Nonlimiting examples of suitable second selective agents include a selective agent selected from the group consisting of a β-lactam antibiotic, an aminoglycoside antibiotic, a quinolone antibiotic, a sulfa antibiotic, a polymyxin antibiotic, and a combination of any two or more of the foregoing antibiotics. In one embodiment, the at least one second selective agent comprises a combination of nalidixic acid, streptomycin, and polymyxin B. Preferably, the concentration of each of the at least one second selective agents in the nutrient medium is selected to permit the growth of a *Salmonella* microorganism. More preferably, the concentration of each of the at least one second selective agents in the nutrient medium is selected to permit the growth of all *Salmonella* microorganisms.

Optionally, compositions of the present disclosure further may comprise a third differential indicator system comprising a third differential indicator compound that is converted by a β-galactosidase enzyme activity to a third detectable product. Third differential indicator systems of the present disclosure comprise a third differential indicator compound that can be converted to a third detectable product by a β-galactosidase enzyme activity. Accordingly, the third differential indicator system distinguishes between microorganisms that produce β-galactosidase enzyme activity and microorganisms that do not produce β-galactosidase enzyme activity. For example, many Salmonellae do not produce β-galactosidase enzyme activity and can be differentiated from the lactose-utilizing members of the Enterobacteriaceae family by using an indicator of β-galactosidase enzyme activity, as disclosed by A. Rambach ("New plate medium for facilitated differentiation of *Salmonella* spp. From *Proteus* spp. And other enteric bacteria", 1990, Appl. Environ. Microbiol., vol. 56, pp. 301-303; which is incorporated herein by reference in its entirety).

However, some reports indicate greater than 90% of the isolated microorganisms from some *Salmonella* species (e.g., *S. bongori*) and subspecies (e.g., *S. enterica arizonae* and *S. enterica diarizonae*) have been found to produce β-galactosidase enzyme activity (for example, see A. M. Littell, "Plating medium for differentiating *Salmonella* arizonae from other Salmonellae", 1977, Appl. Environ. Microbiol., vol. 33, pp. 485-487; which is incorporated herein by reference in its entirety). Thus, a culture medium and/or corresponding procedure designed to distinguish between *Salmonella* microorganisms and non-*Salmonella* microorganisms on the basis of β-galactosidase enzyme activity may erroneously underestimate the number of *Salmonella* microorganisms in a sample if β-galactosidase-producing Salmonellae are present in the sample. The investigators have discovered a method that, surprisingly, is able to distinguish some β-galactosidase-producing *Salmonella* microorganism even when the culture medium used in the method relies on an indicator of β-galactosidase enzyme activity to distinguish between *Salmonella* microorganisms and non-*Salmonella* microorganisms.

Non-limiting examples of suitable third differential indicator compounds according to the present disclosure include 5-bromo-4-chloro-3-indolyl-β-D-galactopyranoside; 5-bromo-3-indolyl-β-D-galactopyranoside; 5-bromo-6-chloro-3-indolyl-β-D-galactopyranoside; 2-nitrophenyl-β-D-galactopyranoside; 3,4-cyclohexenoesculetin-β-D-galactopyranoside; and 4-nitrophenyl-β-D-galactopyranoside. In some embodiments, the third differential indicator system comprises a third differential indicator compound (e.g., lactose) and a pH indicator. In any embodiment, optionally, the composition further can comprise an inducer of β-galactosidase enzyme activity such as isopropyl β-D-1-thio-galactopyranoside (IPTG), for example.

Any embodiment of the composition can be used in a culture device to detect microorganisms in a test sample. Suitable culture devices include, for example, any culture device that is used to hold a nutrient medium in a process to detect microorganisms present in a sample. Nonlimiting examples of suitable culture devices include Petri dishes, multi-well plates, tubes, flasks, thin film culture devices, and the like.

The composition of the present disclosure may be disposed in the thin film culture device in a dehydrated form as disclosed in U.S. Pat. Nos. 4,565,783; 5,601,998; 5,681,712; 6,265,203; and 6,638,755; each of which is incorporated herein by reference in its entirety. In these embodiments, the sample (e.g., an aqueous liquid sample or a solid sample suspended in an aqueous suspending medium) can be brought into contact with the dehydrated components by pipetting the sample into the culture device, for example. In this embodiment, one or more of the components of the composition may be dissolved or suspended in the sample before or after the sample is deposited into the culture device.

Optionally, a culture device (e.g., a thin film culture device) containing a composition of the present disclosure further may comprise a nondifferential indicator system. Suitable nondifferential indicator compounds include indicator compounds that are metabolized by, or otherwise react with, growing microorganisms, and in doing so to produce a fourth detectable product which may cause the microbial colonies or the nutrient medium adjacent the colonies to be colored or fluoresce for ease of visualization, imaging, and/or quantitation. The nondifferential indicator, and the fourth detectable product derived therefrom, should not substantially interfere with the detection of the first detectable product or the second detectable product and/or the third detectable product, if present in the inoculated culture medium. Nonlimiting examples of suitable nondifferential indicator compounds include chromogenic redox indicators such as triphenyl tetrazolium chloride, p-tolyl tetrazolium red, tetrazolium violet, veratryl tetrazolium blue, and 5-bromo-4-chloro-3-indolyl-phosphate disodium salt. The nondifferential indicator system optionally may be provided in an adhesive layer in the thin film culture device as described in U.S. Pat. No. 4,565,783.

In an embodiment, the composition consists essentially of a gelling agent (e.g., any suitable gelling agent as described herein), a nutrient (e.g., any suitable nutrient as described herein) to facilitate the growth of a *Salmonella* microorganism, at least one first selective agent (e.g., any suitable first selective agent as described herein) that inhibits the growth of Gram-positive microorganisms, a first differential indicator system comprising at least one first differential indicator compound (e.g., any suitable first differential indicator system and first indicator compound as described herein), and a second differential indicator system comprising a second differential indicator compound that is converted by urease enzyme activity to a second detectable product (e.g., any suitable second differential indicator system and second differential indicator compound as described herein). In this embodiment, the first differential indicator compound is capable of being converted by a plurality of members of the genus *Salmonella* to a first detectable product. In this embodiment, the first differential indicator compound cannot be converted by a plurality of genera of non-*Salmonella*, Gram-negative enteric microorganisms that form detectable colonies in and/or on the culture medium.

In an embodiment, the composition consists essentially of a gelling agent (e.g., any suitable gelling agent as described herein), a nutrient (e.g., any suitable nutrient as described herein) to facilitate the growth of a *Salmonella* microorganism, at least one first selective agent (e.g., any suitable first selective agent as described herein) that inhibits the growth of Gram-positive microorganisms, a first differential indicator system comprising at least one first differential indicator compound (e.g., any suitable first differential indicator system and first indicator compound as described herein), a second differential indicator system comprising a second differential indicator compound that is converted by urease enzyme activity to a second detectable product (e.g., any suitable second differential indicator system and second differential indicator compound as described herein), and a third differential indicator system comprising a third differential indicator compound that is converted by a β-galactosidase enzyme activity to a third detectable product (e.g., any suitable third differential indicator system and third indicator compound as described herein). In this embodiment, the first differential indicator compound is capable of being converted by a plurality of members of the genus *Salmonella* to a first detectable product. In this embodiment, the first differential indicator compound cannot be converted by a plurality of genera of non-*Salmonella*, Gram-negative enteric microorganisms that form detectable colonies in and/or on the culture medium.

Compositions of the present disclosure can be used in a method of detecting a *Salmonella* microorganism in a sample. Samples tested in the method of the present disclosure include a variety of samples that may be suspected of containing a *Salmonella* microorganism. Samples of particular interest include raw material, in-process material, or finished product material from food-processing or beverage-processing operations. Other suitable samples include, for example, water samples (e.g., surface water, process water), environmental samples (e.g., air samples; surface samples from walls, floors, drains, food-contact surfaces, process equipment); and clinical samples). Non-limiting examples of clinical samples include blood, bile, gastrointestinal samples, rectal samples, and fecal samples. Test samples may include liquids, as well as solid(s) dissolved or suspended in a liquid medium.

Figure 1:
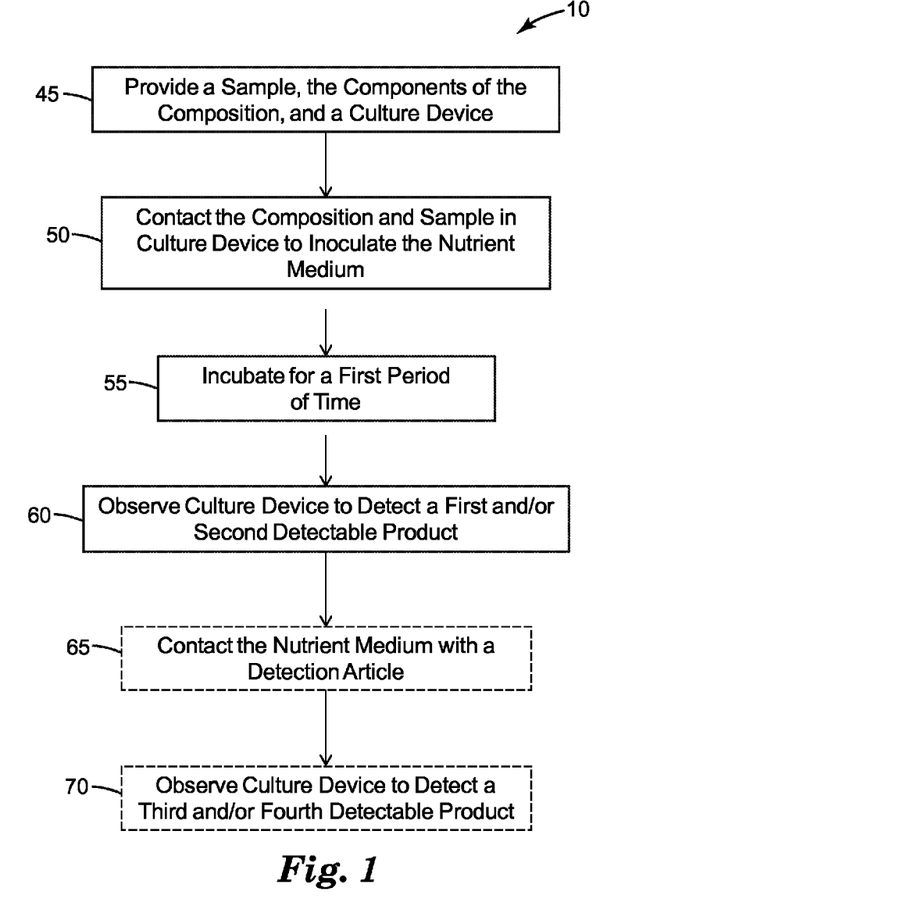
FIG. 1 shows a block diagram of one embodiment of a method of detecting a *Salmonella* microorganism according to the present disclosure.

FIG. 1 shows one embodiment of a method 10 of detecting a *Salmonella* microorganism in a sample according to the present disclosure. The method 10 comprises the step 45 of providing a test sample, the components of the composition, and a culture device. The components of the composition may be provided in the culture device (e.g., as a hydrated composition in a Petri dish; as a substantially water-free, rehydratable coating or plurality of coatings in a thin film culture device) or they may be added to the culture device according to methods that are known in the art.

The method 10 further comprises the step 50 of contacting the composition and the sample to form an inoculated culture device. The sample can be brought into contact in the culture device with the composition in any of a variety of ways. For example, in one embodiment of the method, the composition can be placed into the culture device as a mixture in a hydrated form (e.g., in a hydrated semi-solid culture medium, for example). In this embodiment, the sample (e.g., a liquid sample, a solid sample, a liquid and/or solid sample captured on a filter, a solid sample suspended in a liquid medium) can be deposited and, optionally distributed, into or onto the mixture by techniques that are known in the art such as, for example, pipetting, spread plate inoculation techniques, and streak plate inoculation techniques.

In an alternative embodiment, the sample (e.g., comprising a liquid and/or solid material) is brought into contact and mixed with a liquid mixture (e.g., a molten, tempered liquid agar solution) comprising the composition. If not already present in a culture device, the mixture comprising the sample and the composition is transferred to the culture device.

In yet another alternative embodiment, composition is disposed in a culture device in a dehydrated form, such as in a thin film culture device described herein. A suitable aqueous liquid (e.g., sterile water, a sterile diluent; optionally comprising one or more of the components of the composition) is pipetted into the culture device and the gelling agent is allowed to rehydrate. Subsequently, the sample can be deposited (e.g., by pipetting, streaking, placement of a membrane filter comprising the sample) into the culture device in contact with the composition.

A person having ordinary skill in the art will recognize a variety of other procedures in which the composition can be brought into contact with the sample in a culture device.

Referring back to FIG. 1, the method 10 further comprises the step 55 of incubating the inoculated culture device for a first period of time. Typically, the inoculated culture device is incubated (e.g., in an incubator, an oven, or the like) at an elevated temperature (e.g., about 35-45 degrees C.) to facilitate the growth of enteric microorganisms. In some embodiments, the inoculated culture device is incubated at a temperature of about 37 degrees C. In some embodiments, incubating the culture device can comprise incubating the culture device at a temperature between 41-44 degrees C., inclusive. In some embodiments, wherein the composition comprises an indicator system to detect β-galactosidase enzyme activity, the inoculated culture device may be incubated at a temperature greater than 40 degrees C. to differentiate *Salmonella bongori* from other Gram-negative, enteric microorganisms in the sample, as described in International Publication No WO2013/101530, which is incorporated herein by reference in its entirety.

Unfortunately, some of the reactions that are commonly used to detect groups of non-*Salmonella* enteric microorganisms (e.g. coliform bacteria) do not negatively-differentiate all *Salmonella* strains. For example, there are some *Salmonella* strains that are *lac* positive (produce β-D-galactosidase) and, thus, are not negatively-differentiated from non-*Salmonella* microorganisms in tests that use β-galactosidase enzyme substrates (e.g., 5-bromo-4-chloro-3-indolyl-β-D-galactopyranoside). The investigators have discovered that certain β-D-galactosidase-positive *Salmonella* strains do not react with the β-galactosidase enzyme substrates when incubated at elevated temperatures. In addition, the elevated incubation temperature can inhibit the growth of some non-*Salmonella* β-galactosidase-producing microorganisms and/or does not substantially affect the ability to detect their β-galactosidase enzyme activity. Thus, the present disclosure provides a method for the differentiation of growing colonies of *Salmonella bongori* from colonies of other β-galactosidase-producing enteric microorganisms.

The culture device is incubated for a first period of time sufficient to permit the growth and multiplication of enteric microorganisms present in the sample. Typically, the culture device will be incubated for a first period of at least 6 hours. In some embodiments, the culture devices are incubated for a first period of at least 8 hours. In some embodiments, the culture devices are incubated for a first period of at least 10 hours. In some embodiments, the culture devices are incubated for a first period of about 14 to about 48 hours. In some embodiments, the culture devices are incubated for a first period of about 18 to about 48 hours. In some embodiments, the culture devices are incubated for a first period of about 24 to about 36 hours. In a preferred embodiment, the culture devices are incubated for a first period of about 24±2 h.

The method 10 further comprises the step 60 of observing the culture device to detect a detectable product. The detectable product may be the first detectable product described herein. The first detectable product is an indication of a possible presence of a *Salmonella* microorganism in the test sample. The *Salmonella* microorganism converts the first differential indicator compound (e.g., via fermentation, via metabolic activity, via an enzyme activity) to the first detectable product. Typically, the nutrient medium in the culture device is observed after the first incubation period. In any embodiment, observing the nutrient medium to detect the presence of the first detectable product can comprise observing the culture device to detect a first detectable color. In some embodiments, the first detectable color can be detected by fluorescence (e.g., in an embodiment wherein the first differential indicator compound comprises 4-methylumbelliferyl-α-D-galactopyranoside).

In an embodiment wherein the first differential indicator system comprises a fermentable carbohydrate and a pH indicator, the first detectable color may be a colored zone associated with the pH indicator proximate (e.g., adjacent) a colony of microorganisms capable of converting the carbohydrate to one or more acidic products. In some embodiments, the colony may appear to have the same color as the pH indicator in the surrounding nutrient medium.

In an embodiment wherein the first differential indicator compound comprises a chromogenic enzyme substrate, the first detectable color may be a colored zone proximate to a microorganism colony. For example, the colored zone may comprise a diffusible water-soluble product (e.g., 4-nitrophenol) resulting from a microbial enzyme reacting with the chromogenic substrate (e.g., 4-nitrophenyl-α-D-galactopyranoside). Alternatively, the colored zone may comprise a water-insoluble product (e.g., indigo) resulting from a microbial enzyme reacting with the chromogenic substrate (5-bromo-4-chloro-3-indolyl-α-D-galactopyranoside).

Observing the culture device (step 60) includes observing the culture device to detect the presence or absence of the second detectable product described herein. The second detectable product is produced by the hydrolysis of a urease enzyme substrate by urease enzyme activity that may be associated with a bacterial colony. In some embodiments, the second detectable product may comprise a pH indicator, which changes color in the presence of ammonium hydroxide, a product generated by the hydrolysis of urea by urease enzyme activity in an aqueous liquid. In contrast to the first differential indicator system, which may include, for example, a carbohydrate that is fermented to an acidic product that lowers the pH of the culture medium adjacent the colony reacting with the first differential indicator, a colony reacting with the second differential indicator (e.g., urea) produces enough ammonium hydroxide to raise the pH of the culture medium adjacent the colony, even if the colony is capable of fermenting the first indicator compound to an acidic product. Thus, an observation of the second detectable product (e.g., a colored zone associated with the hydrolysis of urea) adjacent a microbial colony is an indication the colony does not belong to the genus *Salmonella*.

When the third differential indicator system is present in the culture device (e.g., which it is present in the composition), observing the culture device (step 60) includes observing the culture device to detect the presence or absence of the third detectable product described herein. Similarly to the detection of the second detectable product, an observation of the third detectable product (e.g., a colored or fluorescent microbial colony and/or zone adjacent the colony) is an indication the colony does not belong to the genus *Salmonella*.

In some embodiments, the method 10 further can comprise the optional step 65 of contacting the inoculated nutrient medium with a fourth differential indicator system that comprises a third differential indicator compound. The third differential indicator compound that can be converted by a *Salmonella* microorganism to a fourth detectable product and, thus, the fourth differential indicator system functions to confirm the result (i.e., an indication of the presence of a *Salmonella* microorganism) of the first differential indicator system. That is, both the first detectable product and the fourth detectable product provide an indication of the presence of a *Salmonella* microorganism.

The fourth differential indicator compound can be any suitable indicator compound to detect a *Salmonella* microorganism, provided the fourth detectable product derived therefrom is distinguishable; preferably, optically distinguishable, more preferably, visually distinguishable; from the first detectable product of the first differential indicator system, the second detectable product of the second differential indicator system, and the third detectable product of the third differential indicator system. Thus, in one embodiment, the fourth differential indicator system may comprise a pH indicator in conjunction with a nutrient (e.g., a carbohydrate) that can be converted (e.g., via fermentation) to a first detectable product (e.g., an acidic compound such as lactic acid, for example, and/or a gas such as carbon dioxide, for example), as described herein. In another embodiment, the fourth differential indicator system may comprise a chromogenic enzyme substrate, as described herein. In yet another embodiment, the fourth differential indicator system may be a chromogenic enzyme substrate, as described herein. Any first differential indicator system described herein may be suitable for use as a fourth differential indicator system, provided it does not substantially interfere with, and is distinguishable from, the first and second differential indicator systems and/or the fourth indicator system, if present.

Advantageously, the fourth differential indicator system can be used as a means to "confirm" the presence of a *Salmonella* microorganism in the sample. That is, when a presence of a first detectable product is observed in the culture device, that presence can be inferred as an indication of the possible presence of a *Salmonella* microorganism in the sample. However, when a presence of a fourth detectable product is observed in juxtaposition with the presence of the first detectable product (i.e., the first and fourth detectable products are associated with the same bacterial colony); the observation can indicate a higher likelihood (e.g., a significantly higher likelihood) of the presence of a *Salmonella* microorganism in the sample.

After the first incubation period, the fourth differential indicator system can be contacted with the nutrient medium in an inoculated culture device using a variety of procedures including, for example, by contacting an article comprising the fourth indicator system with the nutrient medium. This may be performed, for example, by using an article having a coating comprising the fourth differential indicator system. For example, the article having a coating comprising the fourth differential indicator system may be made using a method similar to that described in U.S. Pat. No. 6,022,682; which is incorporated herein by reference in its entirety.

After the fourth differential indicator system comprising a fourth differential indicator compound is contacted with the inoculated nutrient medium, the method may include the optional step (not shown) of incubating the plate for a second period of time.

Incubating the inoculated culture device for a second period of time can comprise holding the device at an elevated temperature (e.g., in a temperature-controlled incubator). Incubating the inoculated culture device at an elevated temperature (e.g., greater than 25 degrees C. but less than or equal to about 44 degrees C.) can facilitate the conversion by enteric microorganisms (e.g., members of the genus *Salmonella*) of the fourth differential indicator compound to the fourth detectable product. Preferably, incubating the inoculated culture device for a second period of time comprises incubating the culture device at a temperature of 35-42° C., inclusive. In a preferred, incubating the inoculated culture device for a second period of time comprises incubating the culture device at a temperature of 42° C.±1° C.

In some embodiments, the fourth differential indicator system is contacted with the inoculated nutrient medium after the first period of incubation. Advantageously, this may reduce the length of the second incubation period necessary to detect the fourth detectable product. Thus, in some embodiments, the second incubation period can be 1 hour to about 6 hours. In some embodiments, the second incubation period can be about 2 hours to about 5 hours. In a preferred embodiment, the second incubation period is 4 hours±1 hour.

A person having ordinary skill in the art will recognize that, in any embodiment, any one of the first, second, third, or fourth detectable products, if present should not substantially interfere with the detection (e.g., by color masking or fluorescent quenching) of any of the other detectable product. A person having ordinary skill in the art will recognize that, in an embodiment wherein the first, second, third, and/or fourth detectable products are detected by color and/or fluorescence, each detectable product should comprise a chromophore and/or fluorophore that is different (i.e., chromatically-distinguishable) than the other detectable products.

Methods of the present disclosure include observing the culture device to detect a first, second, third, and/or a fourth detectable product. In any embodiment of the method, observing the culture device can comprise observing the nutrient medium in the culture device. In any embodiment of the method, observing the culture device can comprise observing the culture device visually (e.g., using one or more human eyes).

Additionally or alternatively, in any embodiment, observing the culture device can comprise observing the culture device mechanically (e.g., using an imaging system such as, for example, the imaging system described in U.S. Pat. Nos. 6,243,486; 7,496,225; and 7,351,574; each of which is incorporated herein by reference in its entirety. In this embodiment, observing the culture device can comprise creating an image of the culture device using an imaging device. In addition to creating an image of the culture device, the method optionally can comprise analyzing the image using a processor.

Methods of the present disclosure can be used to detect and, optionally, enumerate microorganisms in a sample. For example, observing the presence of the first detectable product in the culture device can indicate a possible presence, in the sample, of a *Salmonella* microorganism (e.g., a member of the species *Salmonella bongori* and/or a member of the species *Salmonella enterica*). However, in methods according to the present disclosure, observing the presence of the first detectable product juxtaposed with the second detectable product indicates a presence of a microorganism other than a *Salmonella* microorganism.

Enumerating microorganisms according to the present disclosure further can comprise enumerating one or more types of microorganisms. The types may be distinguished by their respective reaction, or lack thereof, with any one or more of the indicator systems. Non-limiting examples of types of microorganisms that can be enumerated by the present method include *Salmonella* microorganisms, non-*Salmonella* microorganisms, β-galactosidase-producing microorganisms, and urease-producing microorganisms.

Figure 2:
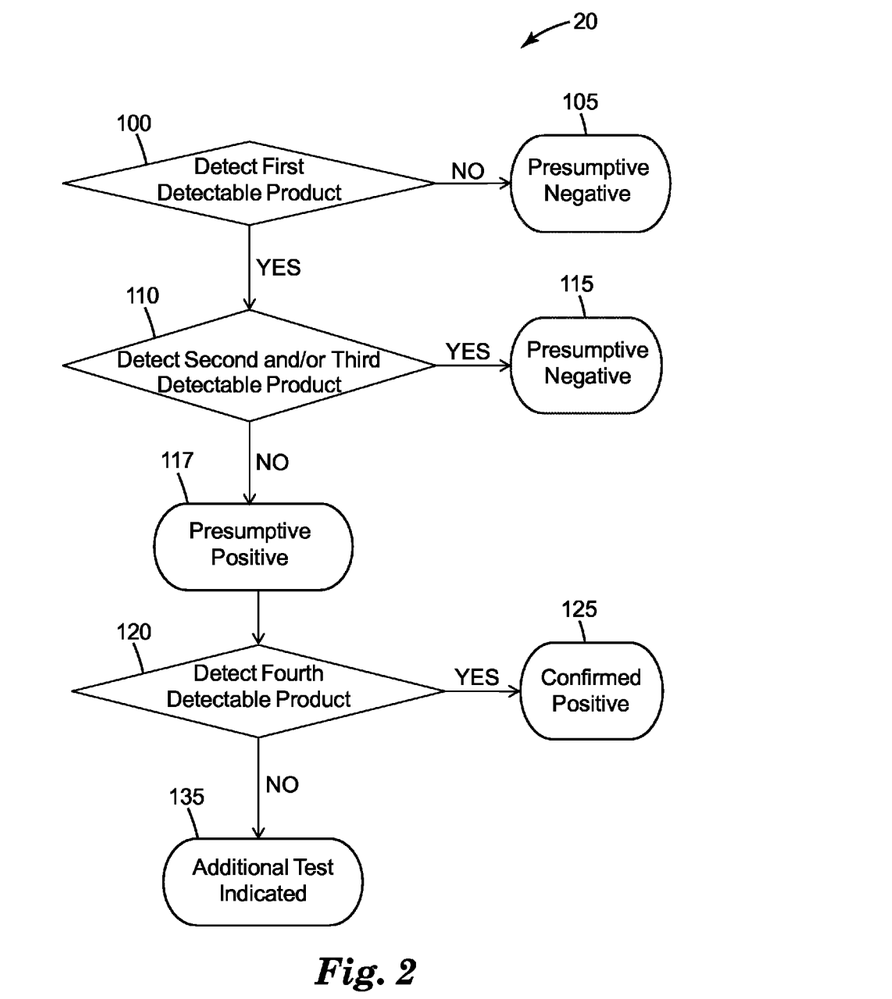
FIG. 2 shows a block diagram of one embodiment of a flow chart used to interpret the results obtained by using the method shown in FIG. 1.

When used according to the present disclosure, the method can detect the presence or absence of a *Salmonella* microorganism in a sample. FIG. 2 shows one embodiment of an analytical flow chart used in conjunction with the results obtained from the method shown in FIG. 1. The flow chart can be used to decide whether any given microbial colony, if substantially pure and spatially separated from other microbial colonies, comprises a member of the genus *Salmonella* or a non-*Salmonella*, Gram-negative enteric microorganism.

After the first incubation period described above, the culture device is observed to detect a presence or an absence of a first detectable product (step 100) and to detect a presence or an absence of a second detectable product (step 110). The first and/or second detectable products can be detected as described herein.

If the first detectable product is not detected after the incubation period, the test sample is presumed not to contain a *Salmonella* microorganism (i.e., the result 105 is considered "Presumptive Negative"). If the first detectable product is observed, the culture device further is observed to detect the presence of the second detectable product juxtaposed with the first detectable product. If the first detectable product and the second detectable product are both observed to be associated with a microbial colony, the microbial colony is presumed not to contain a *Salmonella* microorganism (i.e., the result 115 is considered "Negative").

If the first detectable product is observed to be associated with a microbial colony and the second detectable product is not observed to be associated with the colony, the result 117 is considered "Presumptive Positive" (i.e., the results indicate the colony may belong to the genus *Salmonella*. In this case, the operator may use the fourth differential indicator system described herein to confirm whether the microorganism is a member of the genus *Salmonella*. Thus, after observing a microbial colony to detect the first and second detectable products, the colony is observed to detect the presence or absence of the fourth detectable product (step 120). If the fourth detectable product is observed to be associated with a colony that produces the first detectable product and that does not produce the second detectable product, the result 125 for that colony is considered "Confirmed Positive" (i.e., there are three independent results indicating the microorganism present in the colony belongs to the genus *Salmonella*). If the fourth detectable product is not observed to be associated with a colony that produces the first detectable product and that does not produce the second detectable produce, the result 135 indicates that the microbial colony may or may not belong to the genus *Salmonella* and that additional tests (e.g., genetic tests, immunological tests, biochemical tests) may be used to help identify the microorganism.

EMBODIMENTS

Embodiment 1 is a composition, comprising:
a semisolid culture medium including:
 a gelling agent;
 at least one first selective agent that inhibits the growth of Gram-positive microorganisms;
 a first differential indicator system comprising at least one first differential indicator compound; and
 a second differential indicator system comprising a second differential indicator compound that is converted by urease enzyme activity to a second detectable product;
wherein the first differential indicator compound is capable of being converted by a plurality of members of the genus *Salmonella* to a first detectable product;
wherein the first differential indicator compound cannot be converted by a plurality of genera of non-*Salmonella*, Gram-negative enteric microorganisms that form detectable colonies in and/or on the culture medium.

Embodiment 2 is the composition of Embodiment 1, wherein the first differential indicator compound is a compound selected from the group consisting of melibiose, 2-deoxy-D-ribose, mannitol, L-arabinose, dulcitol, maltose, L-rhamnose, trehalose, D-xylose, sorbitol, and a combination of any two or more of the foregoing compounds.

Embodiment 3 is the composition of Embodiment 1 or Embodiment 2, further comprising a buffer reagent.

Embodiment 4 is the composition of Embodiment 3, wherein the buffer reagent is selected from the group consisting of MOPS, a phosphate salt, TES, HEPES, and combinations thereof.

Embodiment 5 is the composition of any one of the preceding Embodiments, further comprising a third differential indicator system comprising a third differential indicator compound that is converted by a β-galactosidase enzyme activity to a third detectable product.

Embodiment 6 is the composition of Embodiment 5, wherein the third differential indicator compound is a chromogenic enzyme substrate.

Embodiment 7 is the composition of Embodiment 6, wherein the third differential indicator compound is selected from the group consisting of 5-bromo-4-chloro-3-indolyl-β-D-galactopyranoside; 5-bromo-6-chloro-3-indolyl-β-D-galactopyranoside; o-nitrophenyl-β-D-galactopyranoside; p-nitrophenyl-β-D-galactopyranoside; 3,4-cyclohexenoesculetin-β-D-galactopyranoside; and 6-chloro-3-indolyl-β-D-galactopyranoside.

Embodiment 8 is the composition of any one of the preceding Embodiments, wherein the at least one first selective agent is selected from the group consisting of bile salts, cholic acid, deoxycholic acid, crystal violet or a combination of any two or more of the foregoing compounds.

Embodiment 9 is the composition of any one of the preceding Embodiment, wherein the pH indicator is selected from the group consisting of phenol red, chlorophenol red, neutral red, bromthymol blue, and bromthymol purple.

Embodiment 10 is the composition of any one of the preceding Embodiments, further comprising at least one second selective agent that inhibits the growth of at least one Gram-negative enteric microorganism that is not a member of the genus *Salmonella*.

Embodiment 11 is the composition of Embodiment 10, wherein the at least one second selective agent is selected from the group consisting of a β-lactam antibiotic, an aminoglycoside antibiotic, a quinolone antibiotic, a sulfa antibiotic, a polymyxin antibiotic, and a combination of any two or more of the foregoing antibiotics; wherein the concentration of the at least one second selective agent is selected to permit the growth of a *Salmonella* microorganism.

Embodiment 12 is the composition of Embodiment 11, wherein the at least one second selective agent comprises a combination of nalidixic acid, streptomycin, and polymyxin B; wherein a concentration of each of the at least one selective agent in the combination is selected to permit the growth of a *Salmonella* microorganism.

Embodiment 13 is the composition of Embodiment 5, wherein the first selective agent comprises bile salts; the at least one first differential indicator compound comprises 2-deoxy-D-ribose and melibiose; the pH indicator comprises Phenol red, the second differential indicator compounds comprises urea, the third differential indicator compound comprises 5-chloro-4-bromo-3-indoxyl-β-D-galactopyranoside; and the at least one second selective agent comprises naladixic acid, streptomycin, and polymyxin B.

Embodiment 14 is the composition of any one of the preceding Embodiments, wherein the gelling agent is selected from the group consisting of agar, agarose, pectin, gelatin, guar gum, xanthan gum, locust bean gum, hydroxyethylcellulose, carboxymethylcellulose, polyvinyl alcohol, alginate, and a combination of any two or more of the foregoing.

Embodiment 15 is a composition consisting essentially of:
a semisolid culture medium including
 a gelling agent;
 a nutrient to facilitate the growth of a plurality of Gram-negative enteric microorganisms;
 at least one first selective agent that inhibits the growth of a plurality of Gram-positive microorganisms;
 a first differential indicator system comprising at least one first differential indicator compound; and
 a second differential indicator system comprising a second differential indicator compound that is converted by urease enzyme activity to a second detectable product;
wherein the first differential indicator compound is capable of being converted by a plurality of members of the genus *Salmonella* to a first detectable product;
wherein the first differential indicator compound cannot be converted by a plurality of genera of non-*Salmonella*, Gram-negative enteric microorganisms that form detectable colonies in and/or on the culture medium.

Embodiment 16 is a composition, consisting essentially of:
a semisolid culture medium including:
 a gelling agent;
 a nutrient to facilitate the growth of a *Salmonella* microorganism;

at least one first selective agent that inhibits the growth of Gram-positive microorganisms;

a first differential indicator system comprising at least one first differential indicator compound; and a second differential indicator system comprising a second differential indicator compound that is converted by urease enzyme activity to a second detectable product;

wherein the first differential indicator compound is capable of being converted by a plurality of members of the genus *Salmonella* to a first detectable product;

wherein the first differential indicator compound cannot be converted by a plurality of genera of non-*Salmonella*, Gram-negative enteric microorganisms that form detectable colonies in and/or on the culture medium.

Embodiment 17 is a composition, consisting essentially of:

a semisolid culture medium including:
a gelling agent;
a nutrient to facilitate the growth of a *Salmonella* microorganism;
at least one first selective agent that inhibits the growth of Gram-positive microorganisms;
a first differential indicator system comprising at least one first differential indicator compound;
a second differential indicator system comprising a second differential indicator compound that is converted by urease enzyme activity to a second detectable product; and
a third differential indicator system comprising a third differential indicator compound that is converted by a β-galactosidase enzyme activity to a third detectable product;
wherein the first differential indicator compound is capable of being converted by a plurality of members of the genus *Salmonella* to a first detectable product;
wherein the first differential indicator compound cannot be converted by a plurality of genera of non-*Salmonella*, Gram-negative enteric microorganisms that form detectable colonies in and/or on the culture medium.

Embodiment 18 a method of detecting a *Salmonella* microorganism, the method comprising:
providing a test sample, a culture device, and the composition of any one of embodiments 1 through 17;
contacting in the culture device the composition and the test sample to form an inoculated culture device;
incubating the inoculated culture device for a first period of time; and
observing the culture device to detect a first detectable product, wherein the first detectable product is a first indication of a presence of a *Salmonella* microorganism.

Embodiment 19 is the method of Embodiment 18, wherein detecting the first detectable product comprises observing a reaction of the pH indicator with an acidic compound produced by a bacterium.

Embodiment 20 is the method of Embodiment 18 or Embodiment 19, further comprising observing the nutrient medium to detect a second detectable product, wherein the second detectable product indicates a presence of a non-*Salmonella* microorganism.

Embodiment 21 is the method of Embodiment 20, wherein detecting a second detectable product comprises observing a reaction of the pH indicator with a basic compound produced by a bacterium.

Embodiment 22 is the method of any one of Embodiments 18 through 21, further comprising observing the nutrient medium to detect a third detectable product, wherein the third detectable product indicates a presence of a non-*Salmonella* microorganism.

Embodiment 23 is the method of Embodiment 22, wherein detecting the third detectable product comprises detecting a colored product produced by β-galactosidase enzyme activity.

Embodiment 24 is the method of any one of Embodiments 18 through 23, further comprising:
providing an article with a confirmatory indicator compound that can be metabolized by a *Salmonella* microorganism to a fourth detectable product, wherein the fourth detectable product can be distinguished from the first detectable product, second detectable product, and third detectable product, if present;
contacting the article with the culture medium;
incubating the device for a second period of time; and
observing the culture device to detect the fourth detectable product;
wherein detecting the fourth detectable product juxtaposed with the first detectable product is a second indication of the presence in the sample of a *Salmonella* microorganism.

Embodiment 25 is the method of Embodiment 24, wherein incubating the device comprises incubating the device for about 2 hours to about 5 hours.

Embodiment 26 is the method of any one of Embodiments 18 through 25, further comprising enumerating a number of colonies of a first type of microorganisms.

Embodiment 27 is the method of Embodiment 26, further comprising enumerating a number of colonies of a second type of microorganisms.

Embodiment 28 is the method of any one of Embodiments 18 through 27, wherein incubating the culture device comprises incubating the culture device at a temperature between 41-44 degrees C., inclusive.

Embodiment 29 is the method of any one of Embodiments 18 through 28, wherein observing the culture device comprises observing the culture device visually.

Embodiment 30 is the method of any one Embodiments 18 through 29, wherein observing the culture device comprises creating an image of the culture device using an imaging device.

Embodiment 31 is the method of Embodiment 30, further comprising analyzing the image using a processor.

EXAMPLES

Objects and advantages of this invention are further illustrated by the following examples, but the particular materials and amounts thereof recited in these examples, as well as other conditions and details, should not be construed to unduly limit this invention. Unless otherwise indicated, all parts and percentages are on a weight basis, all water is distilled water, and all molecular weights are weight average molecular weight. Pure bacterial cultures were prepared by streaking selected microorganisms on TSA plates (Tryptic Soy Agar Plates with 5% sheep blood; Hardy Diagnostics, Santa Maria, Calif.) and incubating the plates at 37° C. overnight. All microorganism counts were performed according to standard microbiological counting procedures for colony forming units, and counts are approximate numbers.

Materials. Materials, unless otherwise stated are commercially available from Alpha Biosciences, Baltimore, Md. Microorganism cultures listed with an ATCC number were purchased from The American Type Culture Collection (ATCC; Manassas, Va.). Materials utilized in the preparation of the examples are shown in Table 1.

TABLE 1

Materials

| Component | Description | Source |
|---|---|---|
| X-gal | 5-Bromo-4-Chloro-3-Indoxyl-β-D-galactopyranoside | Biosynth AG; Staad, Switzerland |
| IPTG | isopropyl-β-D-thiogalactopyranoside | Sigma-Aldrich; St. Louis, MO |
| Urea | ACS Grade, EMD product # UX0065-1 | EMD Chemicals, Inc.; Gibbstown, NJ |
| Streptomycin sulfate salt | | Sigma-Aldrich |
| Polymyxin B sulfate salt | | Sigma-Aldrich |
| Nalidixic acid sodium salt | | Sigma-Aldrich |

Example 1

Preparation of a *Salmonella* Thin Film Culture Device

A thin film culture device was prepared according to the procedure described in International Publication No. WO2012/161992, which is incorporated herein by reference in its entirety. The powder composition used to prepared the powder-coated paper substrate was made by mixing 2 parts by weight of 2-deoxy-D-ribose (2DDR; Research Products International Corp.; Mt. Prospect, IL) and 98 parts of guar gum (M150 guar MEYPROGAT gum, Meyhall Chemical AG). Before powder-coating, the paper was coated with the adhesive containing TTC.

The broth coating mixture was prepared by adding the materials listed in Table 2 to one liter of deionized water in a container, and was mixed according to the method described in Example 1 of U.S. Pat. No. 6,022,682.

TABLE 2

Ingredients for broth coating mixture.

| Material | Amount (grams) |
|---|---|
| Proteose Peptone No. 3 | 50.0 |
| Porcine Peptone | 14.0 |
| Yeast Extract | 6.0 |
| Sodium Chloride | 10.0 |
| MOPS acid | 3.2 |
| MOPS sodium salt | 5.2 |
| Phenol Red sodium salt | 1.0 |
| Bile Salt No. 3 | 2.0 |
| 5-Bromo-4-Chloro-3-Indoxyl-β-D-galactopyranoside | 0.8 |
| Guar | 14 |

A selective agent mixture was prepared by adding 0.1 g of IPTG, 2.0 g urea, 5.0 g Melibiose (Sigma), 0.005 g Nalidixic acid sodium salt, 0.005 g Streptomycin sulfate salt and 0.00075 g Polymyxin B sulfate salt to 30 ml of sterile deionized water in a 50 mL sterile centrifuge tube and vortexed to mix. The broth mixture was cooled to about 40° C. and the selective agent mixture was added with vigorous mixing. A cover film was prepared by coating the broth onto the corona-treated side of a 2.9 mil polyester film.

The culture device was assembled according to U.S. Pat. No. 6,022,682; with the base member, a foam spacer having a 7.3 cm diameter circle cut from the center to provide a well, and the cover plate adhered together using an adhesive transfer tape. The plates measured approximately 10.3 cm by 10.2 cm with a circular well exposing the dried broth-coated mixture at about the center of the plate.

Example 2

Method of Detecting *Salmonella* Microorganisms

Pure cultures of bacterial strains listed in Table 2, were each inoculated into Buffered Peptone Water (Merck, Darmstadt, Germany) and incubated overnight at 37° C. The resulting bacterial suspensions each had a concentration of approximately $1 \times 10^9$ colony forming units/ml (cfu/ml).

The thin film culture plate of Example 1was prepared for streaking by adding 1.5 mL of sterile Butterfields Phosphate Diluent (Edge Biologicals, Inc.; Memphis, Term.) to about the middle of the well on the powder coating. The cover film was closed, the liquid was spread using a 3M Petrifilm Flat Spreader (3M Company; St. Paul, Minn.) and the gel was allowed to hydrate for about one hour. When the cover film was opened, the broth coating had transferred to the gel surface in the base member. A 10 microliter loop of the bacterial suspension was streaked onto the broth surface on the gel. The cover was closed and the plate was incubated overnight at 42° C. Plates were prepared for each of the bacterial species. The plates were examined for colony growth, colony color and colony zone color. A red- to brown-colored colony (indicating oxidation of the TTC) surrounded by a yellow acid zone (indicating fermentation of 2-deoxy-D-ribose and/or melibiose by the colony) indicates a presumptive positive test result for a *Salmonella* microorganism. A red-purple colony with a purple zone surrounding it (due to the hydrolysis of urea) is a negative test result for a *Salmonella* microorganism. A blue-green colony (indicating hydrolysis of X-gal) with yellow acid zone surrounding the colony indicates the colony may or may not comprise a *Salmonella* microorganism and that additional tests may be indicated. The observations are shown in Table 3.

TABLE 3

Bacterial cultures tested.

| Plate # | Bacteria | Observations |
|---|---|---|
| 1 | *Salmonella typhimurium* (ATCC 14028) | Positive: Red to brown colony with yellow zone around the colony |
| 2 | *Salmonella bongori* (FSD 122) | Positive: Red to brown colony with a yellow zone around the colony |
| 3 | *Salmonella arizonae* (ATCC 42973) | Presumptive Negative: Blue/Green colony with a yellow zone around the colony |
| 4 | *Escherichia coli* (ATCC 25922) | Presumptive Negative: Blue/Green colony with a yellow zone around the colony |
| 5 | *Proteus mirabilis* (ATCC 43071) | Negative: Red to purple colony with a purple zone around the colony |

Example 3

Use of a Detection Article to Detect *Salmonella* Microorganisms

A detection article (disk) was prepared as described in Example 1 of PCT International No. WO2012/092181; which is incorporated herein by reference in its entirety.

Thin film culture devices that contained a presumptive positive result (i.e., plates 1 and 2 from Example 2) were opened and a disk was rolled (to minimize air bubbles) onto the gel surface. The plates were closed and were incubated at 42° C. for 4 hours. The disk was analyzed for color a change adjacent the colonies to confirm whether the colonies reacted with the indicator (5-bromo-4-chloro-3-indolyl-α-D-galactopyranoside) present in the detection article. A change in colony color from red or brown to blue or dark blue indicated the presence of a *Salmonella* microorganism in the colonies. The results of the test are shown in Table 4.

TABLE 4

| Plate # | Bacteria | *Salmonella* ssp. Confirmation Results |
|---|---|---|
| 1 | *Salmonella typhimurium* (ATCC 14028) | Positive: Red to brown presumptive colony with a yellow zone around the colony changed to blue to dark blue colony |
| 2 | *Salmonella bongori* (FSD 122) | Positive: Red to brown presumptive colony with a yellow zone around the colony changed to blue to dark blue colony |

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

Various modifications may be made without departing from the spirit and scope of the invention. These and other embodiments are within the scope of the following claims.

The invention claimed is:

1. A method of detecting *Salmonella* microorganisms comprising:
   providing a test sample, a culture device, and a composition, the composition comprising;
      a semisolid culture medium including
         a gelling agent;
         at least one first selective agent that inhibits the growth of Gram-positive microorganisms;
         a first differential indicator system comprising at least one first differential indicator compound, wherein the at least one first differential indicator compound consists of pH indicator and a fermentable carbohydrate that can be converted by *Salmonella* microorganisms to a first detectable product that comprises an acidic compound or a gas; and
      a second differential indicator system comprising a second differential indicator compound that is converted by urease enzyme activity to a second detectable product; and
      a third differential indicator system comprising a third differential indicator compound that is converted by a β-galactosidase enzyme activity to a third detectable product;
      wherein the first differential indicator compound cannot be converted to the first detectable product by a plurality of genera of non-*Salmonella*, Gram-negative enteric microorganisms that form detectable colonies in and/or on the semisolid culture medium;
   contacting in the culture device the composition and the test sample to form an inoculated culture device;
   incubating the inoculated culture device for a first period of about 14 to about 48 hours;
      wherein incubating the culture device comprises incubating the culture device at a temperature between 41-44 degrees C., inclusive;
   observing the culture device to detect the first detectable product, the second detectable product, and the third detectable product; and
   wherein, after incubating the inoculated culture device for the first period of time, a colony that consists of *Salmonella* microorganisms is identified by its production of an observable quantity of the first detectable product and by its lack of production of an observable quantity of both the second and third detectable products.

2. The method of claim 1, wherein detecting the first detectable product comprises observing a reaction of the pH indicator with an acidic compound produced by a bacterium.

3. The method of claim 1, further comprising observing the semisolid culture medium to detect the second detectable product, wherein the second detectable product indicates a presence of a non-*Salmonella* microorganism.

4. The method of claim 3, wherein detecting the second detectable product comprises observing a reaction of the pH indicator with a basic compound produced by a bacterium.

5. The method of claim 1, wherein detecting the third detectable product comprises detecting a colored product produced by β-galactosidase enzyme activity.

6. The method of claim 1, further comprising enumerating a number of colonies of a first type of microorganisms.

7. The method of claim 6, further comprising enumerating a number of colonies of a second type of microorganisms.

8. The method of claim 1, wherein observing the culture device comprises observing the culture device visually.

9. The method of claim 1, wherein observing the culture device comprises creating an image of the culture device using an imaging device.

10. The method of claim 9, further comprising analyzing the image using a processor.

11. The method of claim 1, wherein a colony that consists of *Salmonella* microorganisms comprises *Salmonella bongori* and/or *Salmonella typhimurium*.

* * * * *

UNITED STATES PATENT AND TRADEMARK OFFICE
CERTIFICATE OF CORRECTION

PATENT NO. : 9,920,350 B2
APPLICATION NO. : 14/368711
DATED : March 20, 2018
INVENTOR(S) : Binsfeld et al.

Page 1 of 1

It is certified that error appears in the above-identified patent and that said Letters Patent is hereby corrected as shown below:

On the Title Page
The first inventor's first name should be "Christine".

In the Specification
Column 2
Line 42 (first occurrence), delete "bromthymol" and insert -- bromothymol --, therefor.
Line 42-43 (second occurrence), delete "bromthymol" and insert -- bromothymol --, therefor.

Column 7
Line 17 (first occurrence), delete "bromthymol" and insert -- bromothymol --, therefor.
Line 17 (second occurrence), delete "bromthymol" and insert -- bromothymol --, therefor.

Column 8
Line 32, delete "bromthymol" and insert -- bromothymol --, therefor.
Line 33, delete "bromthymol" and insert -- bromothymol --, therefor.

Column 12
Line 52, delete "W02013/101530," and insert -- WO2013/101530, --, therefor.

Column 18
Line 4 (first occurrence), delete "bromthymol" and insert -- bromothymol --, therefor.
Line 4 (second occurrence), delete "bromthymol" and insert -- bromothymol --, therefor.
Line 33, delete "naladixic" and insert -- nalidixic --, therefor.
Line 43, delete "including" and insert -- including: --, therefor.

Column 21
Line 15 (approx.), delete "1was" and insert -- 1 was --, therefor.
Line 17 (approx.), delete "Term.)" and insert -- TN) --, therefor.
Line 27 (approx.), delete "W02012/161992," and insert -- WO2012/161992, --, therefor.

Signed and Sealed this
Fourth Day of December, 2018

Andrei Iancu
*Director of the United States Patent and Trademark Office*